US006895600B2

(12) United States Patent
Williams

(10) Patent No.: US 6,895,600 B2
(45) Date of Patent: May 24, 2005

(54) ELASTOMERIC ARTICLE WITH IMPROVED GRIPPING SURFACE

(75) Inventor: Jali Williams, Songkhla (TH)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 26 days.

(21) Appl. No.: 10/029,131

(22) Filed: Dec. 20, 2001

(65) Prior Publication Data

US 2003/0115659 A1 Jun. 26, 2003

(51) Int. Cl.[7] .............................................. A41D 19/00
(52) U.S. Cl. ......................................... 2/161.7; 2/169
(58) Field of Search ........................ 2/159, 160, 161.7, 2/161.3, 167, 168, 169; 264/255, 308; 428/451

(56) References Cited

U.S. PATENT DOCUMENTS

| | | | |
|---|---|---|---|
| 3,813,695 A | | 6/1974 | Podell Jr., et al. |
| 3,883,899 A | | 5/1975 | Ganz |
| 3,969,431 A | * | 7/1976 | Gallagher ............... 260/876 R |
| 4,302,852 A | | 12/1981 | Joung |
| 4,310,928 A | * | 1/1982 | Joung ........................... 2/168 |
| 4,329,312 A | | 5/1982 | Ganz |
| 4,548,844 A | | 10/1985 | Podell et al. |
| 4,598,429 A | | 7/1986 | Mulvaney |
| 4,689,832 A | | 9/1987 | Mulvaney |
| 5,084,514 A | * | 1/1992 | Szczechura et al. ........ 525/123 |
| 5,089,205 A | | 2/1992 | Huang et al. |
| 5,164,231 A | | 11/1992 | Davis |
| 5,196,263 A | | 3/1993 | Melby et al. |
| 5,198,292 A | | 3/1993 | Lerner et al. |
| 5,221,706 A | | 6/1993 | Lee et al. |
| 5,254,391 A | | 10/1993 | Davis |
| 5,272,771 A | * | 12/1993 | Ansell et al. ................... 2/167 |
| 5,284,607 A | * | 2/1994 | Chen ........................... 264/37 |
| 5,302,440 A | | 4/1994 | Davis |
| 5,534,350 A | * | 7/1996 | Liou ............................. 2/168 |
| 5,571,219 A | | 11/1996 | Gorton |
| 5,654,093 A | | 8/1997 | Kidon et al. |
| 5,691,069 A | | 11/1997 | Lee |
| 5,700,585 A | | 12/1997 | Lee |
| 5,712,346 A | | 1/1998 | Lee |
| 5,742,943 A | | 4/1998 | Chen |
| 5,881,386 A | | 3/1999 | Horwege et al. |
| 5,886,089 A | | 3/1999 | Knowlton |
| 5,985,955 A | | 11/1999 | Bechara et al. |
| 5,993,923 A | | 11/1999 | Lee |
| 6,016,570 A | * | 1/2000 | Vande Pol et al. ............... 2/168 |

FOREIGN PATENT DOCUMENTS

| | | |
|---|---|---|
| EP | 0482618 | 4/1992 |
| EP | 1036810 A2 | of 2000 |
| EP | 1036810 A3 | 11/2000 |
| WO | WO 8808311 | 11/1988 |
| WO | WO 9114461 | 10/1991 |
| WO | WO 9114462 | 10/1991 |
| WO | WO 0035978 | 6/2000 |

OTHER PUBLICATIONS

Material Safety Data Sheet for Acrylic Polymer Coating for DEV–3537, AE–3392PMN TYPE dated Jun. 12, 2000.
PCT Search Report, Jan. 2, 2003.

*Primary Examiner*—Gary L. Welch
(74) *Attorney, Agent, or Firm*—Dority & Manning, P.A.

(57) ABSTRACT

The present invention is directed to the production of elastomeric articles, such as elastomeric gloves, which can be easily stripped from forming molds, provide good tactile and gripping characteristics, and can be powder free with no halogenation or surface treatments. In general, the elastomeric articles of the invention include an ultra-thin outer layer formed of an acrylic-based polymer and a base polymer layer coagulated onto the surface of the outer layer which forms the primary matrix of the elastomeric article. The ultra-thin outer layer of the articles can be between about 0.25 microns and about 8.0 microns thick.

29 Claims, 3 Drawing Sheets

U.S. PATENT DOCUMENTS 6,019,922 A * 2/2000 Hassan et al. .............. 264/130
6,040,365 A    3/2000 Theders
6,075,081 A    6/2000 Nile et al.
6,156,424 A   12/2000 Taylor
6,284,856 B1   9/2001 Lee
6,347,408 B1 * 2/2002 Yeh ................................ 2/167
6,391,409 B1 * 5/2002 Yeh et al. ...................... 2/168
6,465,591 B1  10/2002 Lee

* cited by examiner

ELASTOMERIC ARTICLE WITH IMPROVED GRIPPING SURFACE

BACKGROUND OF THE INVENTION

Elastomeric articles made from natural or synthetic rubber are used in many different applications including being used as surgeons gloves, examining gloves, prophylactics, catheters, balloons, tubing, and the like. Elastomeric materials have been useful in the production of such articles because of their physical properties. For example, these materials exhibit very elastic properties. The materials not only can be stretched many times their length, but are also capable of substantially returning to their original shape when released.

Traditionally, elastomeric articles have been manufactured through the use of a mold or former in the shape of the final article to be produced. For example, when manufacturing a glove, a hand-shaped mold or former is first dipped in a coagulant slurry containing calcium nitrate and calcium carbonate. After the slurry has dried on the former, the former is dipped in an elastomeric material such as a natural or synthetic latex such that a coating is coagulated on the former. The formed elastomeric article is then cured and cooled and stripped from the mold which turns the glove right side out.

Elastomeric articles are typically tacky to the touch when initially manufactured. The tackiness increases the difficulty in handling the glove during manufacture, packaging, and final use. Difficulties encountered include problems in stripping the product from the mold during manufacture, products sticking to each other during packaging, and, when gloves are produced, problems with donning the gloves and gripping and feeling articles when wearing the gloves. As a result, elastomeric articles are usually further processed to reduce their tackiness. Historically, the most common process for reducing tackiness has been the application of a powder such as cornstarch to the surfaces of the glove. While the use of a powder is acceptable for some applications, powders may not be used in certain applications, such as surgical or other clean room type applications.

As a result, powder free processing techniques have been developed. For example halogenation, such as chlorination, and other chemical surface treatments have been developed in order to eliminate powders on the product. However, these powder free techniques tend to not only be expensive, but may also reduce the shelf life of the treated elastomeric article. Other methods of forming a powder-free glove, such as the methods disclosed in U.S. Pat. No. 5,993,923 to Lee, which is incorporated herein by reference, can include forming a powder free polymeric coating on the glove. These coatings can be relatively thick, however, from about 10 to about 25 microns on one or both surfaces of the glove. Such thick coatings can interfere with tactile sensitivity necessary when wearing the gloves, as well as interfere with the desired characteristics, such as the stretching and modulus characteristics, of the primary matrix forming the glove body.

Another problem experienced with elastomeric articles in the past is that the outer surfaces may become slippery when they are wet, and the wearer may find it more difficult to grasp objects in the gloved hand without losing the grip. This problem is particularly troublesome for gloves treated by powder-free processing techniques, because the very processing which reduces tackiness on the surface of the glove can also promote excessive loss of gripping ability.

Thus, a need exists for a powder free elastomeric article which may be easily stripped from the forming mold and has good gripping and tactile characteristics, while retaining the desired characteristics of the primary matrix forming the body of the article.

SUMMARY OF THE INVENTION

In general, the present invention is directed to elastomeric articles and a process for producing elastomeric articles. More specifically, the present invention is directed to the production of elastomeric gloves.

The elastomeric articles of the present invention can include an ultra-thin outer layer formed of an acrylic-based polymer. The outer layer of the article can be between about 0.25 and about 8 microns thick. Specifically, the outer layer of the article can be between about 0.5 and about 5 microns thick. More specifically, the outer layer can be between about 0.5 and about 1.5 microns thick. In an embodiment wherein the elastomeric article is a glove, the ultra-thin outer layer can be an ultra-thin gripping layer.

Adjacent to and attached to the ultra-thin outer layer of the elastomeric articles of the present invention can be a base polymer layer. The base polymer layer can be coagulated onto the surface of the ultra-thin outer layer. In general, the base polymer layer can be thicker than the ultra-thin outer layer. For example, the base polymer layer can be between about 3 and about 10 mils thick. The base polymer layer can include an elastomeric material, for example, a natural latex rubber or a synthetic elastomer such as a nitrile polymer.

As described above, the base polymer layer of the elastomeric article can be coagulated onto the surface of the ultra-thin outer layer of the article. In certain embodiments of the present invention, a coagulant composition can be coated on the ultra-thin outer layer between the outer layer and the base polymer layer. Thus, the base polymer layer can coagulate upon contact of the base polymer layer with the coagulant composition.

In certain embodiments, the coagulant composition can contain a metal salt and a surfactant. More specifically, the metal salt of the coagulant composition can include calcium nitrate.

In one embodiment, the elastomeric article of the present invention can also include an inner layer. The inner layer can be attached and adjacent to the base polymer layer such that the base polymer layer is between the inner layer and the outer layer. In an embodiment wherein the elastomeric article is an elastomeric glove, the inner layer can be a donning layer.

The present invention is also directed to a process for producing an elastomeric glove. The process of the present invention can include forming an ultra-thin gripping layer on a glove-shaped former such as by dipping. The ultra-thin gripping layer of the glove can be between about 0.25 and about 8.0 microns thick. The gripping layer of the glove can include an acrylic-based polymer. After the acrylic-based polymer is formed, the gripping layer can be contacted with a coagulant composition. A base polymer layer can then be formed on the ultra-thin gripping layer. The base polymer layer can include an elastomeric material which can coagulate upon contact of the elastomeric material with the coagulant composition. The base polymer layer can be formed through one or more dipping steps wherein the glove-shaped former is dipped into one or more tanks containing the elastomeric material of the base polymer layer.

In one embodiment of the present invention, an emulsion containing the acrylic-based polymer which forms the ultra-thin gripping layer of the glove can be heated to a temperature of between about 35° C. and about 50° C. prior to the formation of the ultra-thin gripping layer. In one embodiment, besides the acrylic-based polymer, the emulsion can contain at surfactant, such as a nonionic surfactant, having a hydrophilic-lipophilic balance (HLB) of between about 7 and about 11.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

DETAILED DESCRIPTION

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to the production of powder free elastomeric articles having good stripping, tactile and gripping characteristics. More specifically, the elastomeric articles of the present invention can be powder free elastomeric articles which can be easily stripped from the forming molds, provide good sensitivity and gripping abilities to the final product, and do not require any additional powder free processing techniques, such as halogenation (i.e., chlorination) or other chemical surface treatments. Though the elastomeric articles referred to in the remainder of this description are generally referred to as gloves, it should be understood that the present invention is applicable to other elastomeric articles as well, and is not to be limited to gloves.

In general, according to the present invention, the elastomeric articles include an exterior coating of an acrylic-based polymer. When forming gloves, the acrylic-based polymer is used to form an exterior gripping surface on the glove. In accordance with the present invention, the acrylic-based polymer is applied to the glove as an ultra-thin coating, having a thickness of less than about 8 microns. The acrylic-based polymer coating is located adjacent to a base polymer layer in order to form the elastomeric article, such as the glove. The base polymer layer can be any suitable elastomeric material, such as a natural latex rubber or a nitrile rubber.

In one embodiment of the present invention, a former or mold is used to form the elastomeric article. The acrylic-based polymer layer is first formed on the former. Subsequently, the base polymer layer is formed. For example, the acrylic-based polymer layer can be formed followed by application of a coagulant. After the coagulant has been applied to the former, the former can be contacted with an elastomeric material that coagulates and forms the base polymer layer.

Various advantages and benefits are realized by first forming the thin acrylic-based polymer layer followed by application of the coagulant and the base polymer layer. For instance, it is believed that very thin coatings can be formed by applying the acrylic-based polymer to the former in a separate step from the coagulant composition. The coagulant composition can also contain powders which become encased within the elastomeric article for forming powderless products.

Figure 1:
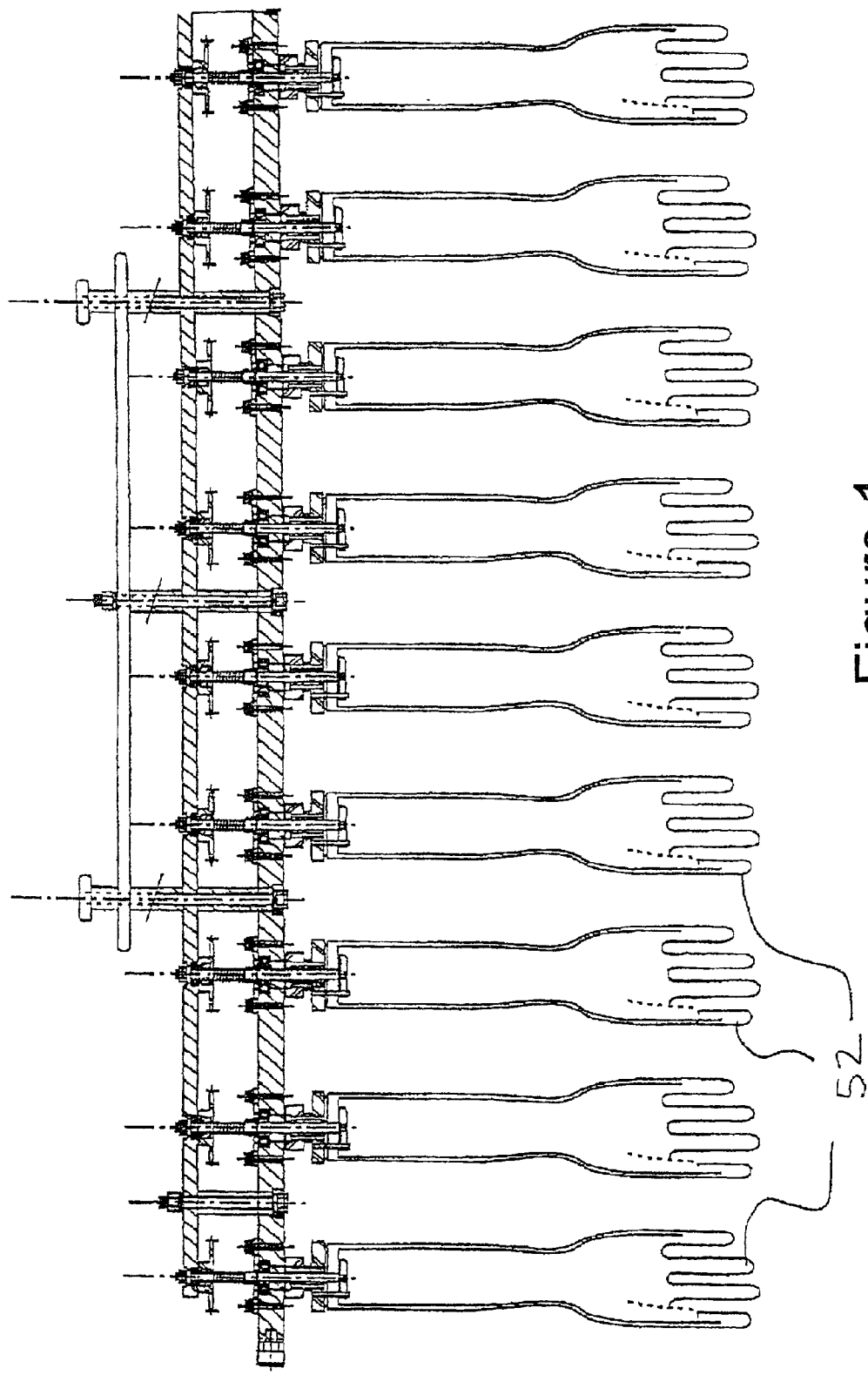
FIG. 1 is an illustration of glove-shaped formers that may be used in accordance with one embodiment of the present invention.

FIG. 1 is an illustration of a series of glove molds or formers 52 which may be used to form the elastomeric gloves of the present invention. The formers 52 shown in FIG. 1 are illustrated on a pallet as is conventionally used in a batch processing operation, but it should be understood that the process of the present invention may equally be utilized in a continuous operation. A former 52 can generally be a contoured mold having a textured or smooth surface which can accept a series of coatings and release the formed glove. Possible materials for the surface of former 52 can include any suitable surface material. For example, the surface of former 52 can be formed of ceramic, porcelain, glass, metal, or certain fluorocarbons.

In general, a former 52 can be cleaned prior to formation of a glove on the former. The cleaning process can generally include an optional water pre-rinse followed by an acid wash. After the acid wash, the former 52 can be rinsed with water and dipped in a heated caustic solution prior to a final rinse. After the optional cleaning process, a glove can be formed on the former 52 through a series of dipping and drying steps.

Figure 2:
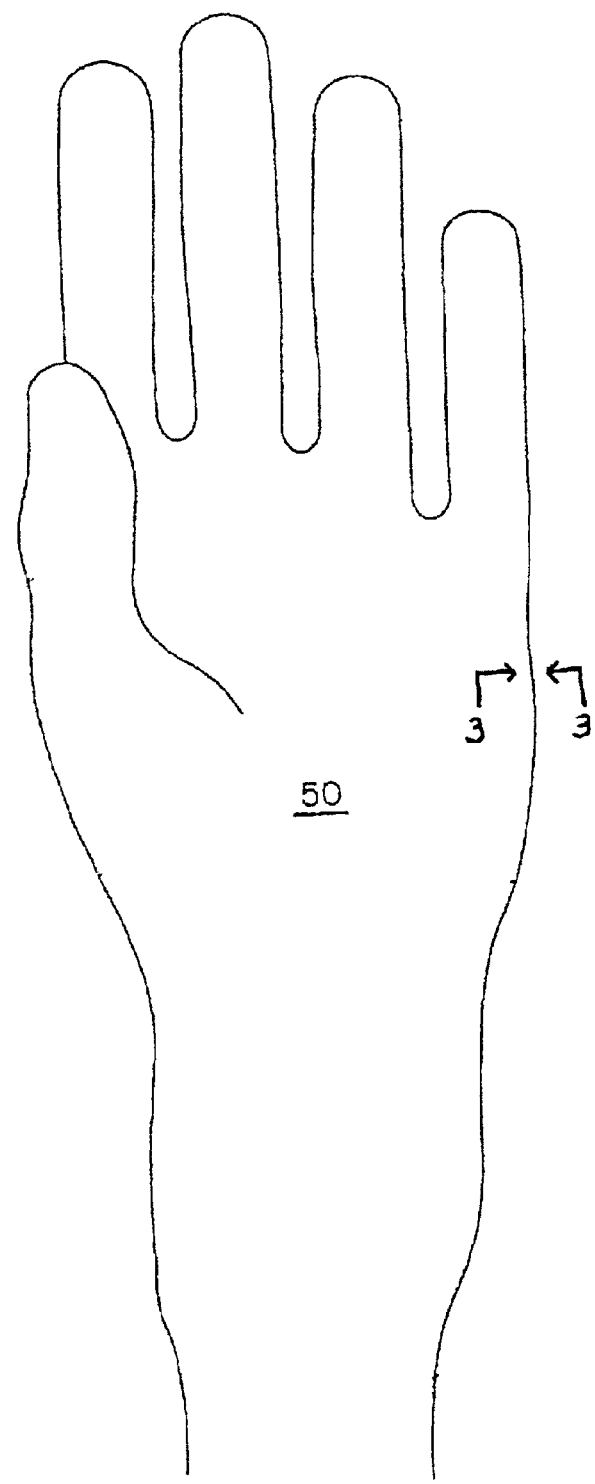
FIG. 2 is a front view of a glove according to the present invention.

FIG. 2 illustrates one possible embodiment of a glove 50 which can be formed on former 52. The glove 50 can be powder free and still maintain good stripping and tactile characteristics. In one embodiment, the glove 50 can be formed through a series of dippings or immersions of the former 52. For example, in one embodiment, the former 52 can first be dipped in a polymer emulsion, particularly an emulsion containing an acrylic-based polymer, to form a gripping layer. Following the gripping layer polymer emulsion dip, the former 52 can be dipped in a coagulant composition followed by one or more base polymer dips which can form the primary matrix of the glove. Subsequent to any desired finishing processes, such as vulcanization, purification, and/or addition of a donning layer to the glove, for example, the glove 50 can be stripped from the former 52. The stripping process can turn the glove right side out and place the first-formed gripping layer on the outer surface of the finished glove 50. In one embodiment of the invention, the gripping layer can provide good stripping characteristics to the glove in order to easily remove the glove 50 from the former 52 after formation and can also be an ultra-thin gripping layer on the outer surface of the finished glove.

The ultra-thin gripping layer of the present invention can provide good gripping characteristics to a glove, enabling the wearer to securely grip and hold instruments such as, for example, surgical instruments, dental instruments, manufacturing instruments, and the like. In addition, the ultra-thin gripping layer of the glove can provide good gripping characteristics to the glove without an attendant loss in either tactile sensitivity for the wearer or physical characteristics, such as elongation and modulus characteristics, of the base polymer which forms the primary matrix of the glove.

Maintaining good tactile sensitivity while wearing a glove can be crucial in certain embodiments such as surgical or manufacturing applications. There are many applications involving the use of elastomeric gloves wherein the glove wearer must maintain a good sense of touch in the fingers in spite of the glove covering on the fingers. For example, tactile sensitivity can be important in order to control the fine motor motion necessary to properly manipulate tools in a manufacturing or medical application. Similarly, a lack of tactile sensitivity can prevent a glove wearer from properly feeling what the fingers may encounter, such as tissue abnormalities in a medical application. A relatively thick coating on either the inside or outside of a glove can interfere with the sense of touch of the wearer or interfere with the properties of the primary matrix. Unnecessarily thick layers of a glove can cause what may be vital tactile sensitivity to be impaired. Thus, an ultra-thin gripping layer, such as that of the present inventive gloves, can be very beneficial to the wearer.

In addition to improved tactile sensitivity, the ultra-thin gripping layer of the present invention can provide a good gripping surface on a glove without an accompanying detrimental loss of physical characteristics, such as, for example, elongation and modulus characteristics, of the primary matrix forming the glove body. A thick coating on an elastomeric glove can interfere with such properties and inhibit the wearer from performing necessary tasks.

The ultra-thin gripping layer of the present invention can generally be formed by dipping the former 52 into an emulsion which includes an acrylic-based polymer. The acrylic-based polymer emulsion can be prepared from any suitable acrylic-based polymer.

For example, in one embodiment, the acrylic-based polymer emulsion can be formed with an acrylic-based copolymer. It is believed that the acrylic-based copolymer can include at least one reactive low surface energy monomer (preferably one or more copolymerizable silicone oligomers), at least one alkyl acrylate and at least one hard monomer. By the term low surface energy monomer is meant a copolymerizable monomer which, if homopolymerized, can be released from a surface with a relatively low level of force. Examples of a low surface energy monomer can include reactive silicones, fluorocarbons, fatty acid esters, and the like having vinyl, acrylic and/or methacrylic functionalities. Alkyl acrylate monomers which can be used in the acrylic based copolymer can be alkyl acrylate monomers containing from 1 to about 10 carbon atoms in the alkyl group, present in a total amount of from about 30% to about 85% by weight of the monomers. Possible alkyl acrylate monomers can include methyl acrylate, ethyl acrylate, butyl acrylate, propyl acrylate, 2-ethylhexyl acrylate, isooctyl acrylate, isodecyl acrylate, and the like. Hard monomers are monomers which, if homopolymerized, would have glass transition temperatures greater than about 25° C. Possible hard monomers for use in forming the copolymer can include styrenic monomers such as styrene, alpha methyl styrene and the like; alkyl methacrylates, such as methyl methacrylate, ethyl methacrylate, butyl methacrylate and the like; and amides, such as an n-isobutoxymethyl acrylamide and the like. Examples of such acrylic-based copolymers for use in forming the acrylic-based polymer emulsion are further described in U.S. Pat. No. 5,993,923 to Lee, U.S. Pat. No. 5,712,346 to Lee, and U.S. Pat. No. 5,691,069 to Lee which are all herein incorporated by reference thereto.

In one embodiment of the present invention, an acrylic-based polymer emulsion is prepared using an acrylic-based polymer sold by the Avery Dennison Corporation under the product name of DEV-3537PMN or DEV-3538. The acrylic-based polymer is usually supplied in the form of a high solids content emulsion which can then be dispersed in a dip tank with water to form a polymer emulsion of somewhat lower solids content. For example, the solids content of the tank after dispersion of the emulsion can be between about 2% and about 6% solids concentration by weight. More specifically, the polymer emulsion can have between about 3% and about 6% solids concentration by weight.

In certain embodiments of the present invention, a surfactant can also be added to the concentrated acrylic-based polymer emulsion prior to dispersing the polymer in a dip tank. For example, a surfactant can be added to the concentrated acrylic polymer emulsion in an amount from about 0.1% to about 0.2% w/w. Suitable surfactants can increase emulsion stability and improve wetting characteristics of the emulsion.

One system commonly used to predict surfactant properties in order to aid in determining suitable surfactants is the hydrophilic-lipophilic balance (HLB) system. The HLB system is based on the concept that some molecules have hydrophilic groups, other molecules have lipophilic groups, and some have both. Weight percentage of each type of group on a molecule or in a mixture predicts what behavior the molecular structure will exhibit. A number on a scale of one to 40 can be determined for a specific compound or mixture according to the semi-emperical method introduced by W. C. Griffin (1949 and 1954). More detailed information on the HLB system can be found in "Classification of Surface-Active Agents by 'HLB'," *Journal of the Society of Cosmetic Chemists* 1, Griffin, W. C., (1949):311; "Calculation of HLB Values of Non-Ionic Surfactants," *Journal of the Society of Cosmetic Chemists* 5, Griffin, W. C., (1954) :259; and "How to Determine HLB of an Emulsifier," ICI Americas, Inc., Wilmington, Del., 1992. All of which are incorporated herein by reference thereto.

For example, a suitable surfactant that can be added to the concentrated acrylic polymer emulsion can have an HLB of between about 7 and about 11. More specifically, an added surfactant can have an HLB of about 9. In some embodiments, the surfactant can be a non-ionic surfactant. One possible example of a surfactant which can be added to the concentrated acrylic-based polymer emulsion is SUR-FYNOL TG which can be obtained from the Air Products Corporation.

It may be desired to heat the acrylic polymer emulsion prior to dipping the glove formers in the tank, though this is not critical to the present invention. When heating of the acrylic-based polymer emulsion is desired, the emulsion can be heated to between about 35° C. and about 50° C.

A former 52 can be dipped in the acrylic-based polymer emulsion in order to form an ultra-thin polymer layer on the surface of the former 52 which can be the ultra-thin outer, or gripping, layer of the finished elastomeric product. The polymer coating should be thin in order to provide a good gripping surface to a glove while limiting loss of wearer sensitivity and elastic properties of the primary matrix material. For example, the ultra-thin outer layer formed from the acrylic-based polymer can be between about 0.25 and about 8 microns thick. Specifically, the ultra-thin outer layer can be between about 0.5 and about 5 microns thick. More specifically, the ultra-thin outer layer can be between about 0.5 and about 1.5 microns thick.

After dipping or immersing a former 52 in a tank containing the acrylic-based polymer emulsion, the acrylic-based polymer can be dried on the former before further processing. Any suitable drying method can be employed. For many applications, the acrylic-based polymer can be air dried.

After drying, the former 52 can be dipped in a coagulant composition prior to being dipped in a base polymer emulsion for formation of the primary matrix of the glove body. It has been found that a separate dip step for the coagulant composition after the ultra-thin gripping layer has been dried improves the inventive gloves. For example, in the past, an acrylic-based polymer and a coagulant composition have been combined in a mixed emulsion for coating a former in one dip step. However, such mixed emulsions have been found to be unstable, and both the coagulant salt and the acrylic-based polymer can come out of solution. This can lead to the undesired formation of small masses of the polymer and/or the salt in the finished glove. Hence, separate dips for the acrylic polymer composition and the coagulant composition are preferred in forming the gloves of the present invention.

In addition, it is believed that thinner coatings can be formed by applying the acrylic-based polymer composition to the former separate from the coagulant composition. Further, coagulant compositions can sometimes contain powders and other particles. By applying the coagulant composition between the exterior layer and the base polymer layer, any particles or powders contained within the coagulant composition become trapped inside the matrix of the glove for forming powderless gloves without the need for subsequent processing steps.

A coagulant causes the base polymer to coagulate and polymerize. Coagulants that may be used in the present invention can include a solution of a coagulant salt such as a metal salt. Examples of coagulants that can be used include water soluble salts of calcium, zinc, aluminum, and the like. For example, in one embodiment, calcium nitrate in water or alcohol can be used in the coagulant composition. In such an embodiment, calcium nitrate can be present in the solution in an amount of up to about 40% by weight. Optionally, the coagulant composition can also contain additives such as surfactants. In one embodiment, the coagulant composition can include the following:

| | |
|---|---|
| Calcium nitrate (77%) | 18.75 wt % |
| SURFYNOL TG (non-ionic surfactant) | 0.15 wt % |
| Teric 320 (10%) (non-ionic surfactant) | 1.37 wt % |
| SURFONYL DF 37 (non-ionic surfactant) | 0.005 wt % |
| Water | remainder |

After being immersed into the coagulant composition, the former 52 can be withdrawn and the coagulant present on the surface of the ultra-thin gripping layer can be allowed to dry. For many applications, the coagulant can be air dried for a time of from about one minute to about two minutes. Once dried, a residual coating of the coagulant is left on the gripping layer.

Next, the former 52 coated with the acrylic-based polymer and the coagulant can be immersed or dipped into a base polymer emulsion. The coagulant in the coagulant composition causes some of the base polymer to become locally unstable and coagulate on the surface of the acrylic-based gripping layer. Thus the coagulant composition does not form a separate layer in the final glove, but rather becomes a part of the base polymer layer forming the primary matrix of the glove. The amount of time the former 52 is immersed (commonly termed as dwell time) in the base polymer emulsion determines the thickness of the film. Increasing the dwell time of the former in the polymer causes the thickness of the film to increase. After the desired amount of time, the former 52 is withdrawn from the base polymer emulsion, and the coagulated base polymer layer is allowed to coalesce fully on the ultra-thin gripping layer.

The base polymer of the present invention can be any suitable flowable elastomer. Possible elastomeric materials can include a natural latex rubber or a synthetic elastomer, such as a nitrile polymer. Further elastomers include, for example, styrene butadiene, neoprene, isoprene, styrene-ethylene-butylene-styrene (S-EB-S), styrene-isoprene-styrene (S-I-S), styrene-polybutydiene-styrene (S-B-S), or polyvinyl chloride (PVC). The above elastomeric materials can be formulated into suitable dipping solutions or emulsions into which a former can be dipped for forming the base polymer layer. In some embodiments, such as when forming a polyvinyl chloride glove, a coagulant composition may not be needed.

Once the former 52 is removed from the base polymer emulsion, the base polymer present on the ultra-thin gripping layer can be further processed, as desired. For example, the base polymer layer can be gelled with heat to strengthen the elastomeric film, leached with flowing hot water to remove impurities, and cured, though specific finishing processes can depend upon the make up of the base polymer emulsion.

After the base polymer film is dried, additional layers of the base polymer can be applied to the former 52, as desired. If desired, the former 52 can once again be immersed or dipped into the base polymer emulsion in order to increase the thickness of the primary matrix of the glove. The total matrix thickness can depend on many parameters including, for example, the number of times the former is immersed into the base polymer emulsion and make up of the base polymer emulsion. The total thickness of the base polymer layer of the glove can be anywhere from about 3 mil to about 10 mil, particularly from about 3 mil to about 5.5 mil.

Figure 3:
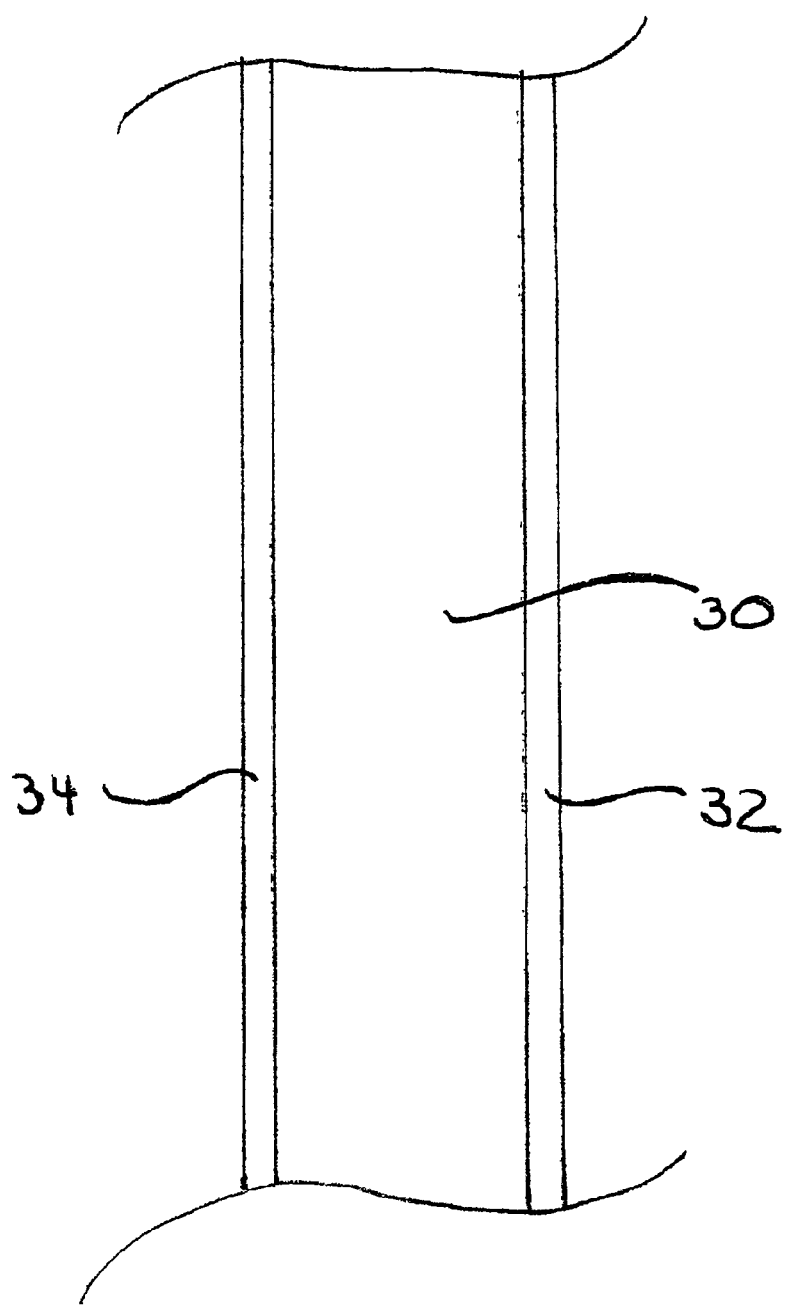
FIG. 3 is an enlarged cross-sectional view of one embodiment of an elastomeric article of the present invention.

If desired, after the base polymer layer is formed, the former can be dipped into other solutions for forming other coatings on the article. For example, when forming gloves, other coatings can be placed on the glove for facilitating donning of the glove. FIG. 3 is an illustration of a cross section of a portion of an article made according to the present invention containing three distinct layers. Though not to scale, the base polymer layer 30 can be much thicker than the ultra-thin outer layer 32 on the outside of the article. The article of FIG. 3 also includes another layer 34 on the opposite side of the article from the outer layer 32 such that the base polymer layer 30 is sandwiched between the ultra-thin outer layer 32 on the outside of the article and an inner layer 34.

In an embodiment involving formation of a glove, the inner layer 34 can be a donning layer. Possible donning layers can be formed of any suitable material. For example, a donning layer 34 can also be formed from an acrylic-based polymer. In this embodiment, the former 52 can be again dipped or immersed in a polymer emulsion used to form the donning layer subsequent to formation of the base polymer layer 30. However, the presence of an inner/donning layer 34 is not a requirement of the present invention. Also, any other donning layer which is known in the art, such as a polyurethane coating, a silicone coating, or a hydrogel coating, for example, can be employed in the present invention.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An elastomeric article comprising:
   an ultra-thin outer layer comprising an acrylic-based polymer, said ultra-thin outer layer being between about 0.25 and about 1.5 microns thick; and
   a base polymer layer adjacent and attached to said ultra-thin outer layer, said base polymer comprising an elastomeric material which has been coagulated on said ultra-thin outer layer.

2. The elastomeric article of claim 1, wherein said elastomeric material is selected from the group consisting of a natural latex rubber and a synthetic elastomer.

3. The elastomeric article of claim 1, wherein said ultra-thin outer layer is between about 0.5 and about 1.5 microns thick.

4. The elastomeric article of claim 1, wherein said base polymer layer is between about 3 mils and about 5.5 mils thick.

5. The elastomeric article of claim 1, wherein said elastomeric article is a glove.

6. The elastomeric article of claim 5, wherein said glove further comprises an inner layer, said inner layer being attached and adjacent to said base polymer layer such that said base polymer layer is between said ultra-thin outer layer and said inner layer.

7. The elastomeric article of claim 1, wherein said elastomeric material has been coagulated through contact of said elastomeric material with a coagulant composition, said coagulant composition being applied to said ultra-thin outer layer between said ultra-thin outer layer and said base polymer layer.

8. The elastomeric article of claim 7, wherein said coagulant composition comprises calcium nitrate.

9. The elastomeric article of claim 1, wherein the article is not chlorinated.

10. A glove comprising:
    an ultra-thin gripping layer comprising an acrylic-based polymer, said ultra-thin gripping layer being between about 0.25 and about 1.5 microns thick; and
    a base polymer layer, said base polymer layer comprising an elastomeric material selected from the group consisting of a natural latex rubber and a synthetic elastomer, said elastomeric material being coagulated onto said ultra-thin gripping layer through contact of said elastomeric material with a coagulant composition, said coagulant composition being applied to said ultra-thin gripping layer between said ultra-thin gripping layer and said base polymer layer.

11. The glove of claim 10, further comprising a donning layer adjacent to and attached to said base polymer layer such that said base polymer layer is between said ultra-thin gripping layer and said donning layer.

12. The glove of claim 10, wherein said base polymer layer is between about 3 mils and about 5.5 mils thick.

13. The glove of claim 10, wherein said coagulant composition comprises calcium nitrate.

14. The glove of claim 10, wherein said glove is a powder free glove.

15. The glove of claim 10, wherein the glove is not chlorinated.

16. The glove of claim 10, wherein the base polymer layer comprises a natural latex rubber.

17. The glove of claim 10, wherein the base polymer layer is a nitrile polymer.

18. The glove of claim 10, wherein said ultra-thin outer layer is between about 0.5 and about 1.5 microns thick.

19. A process for producing a glove comprising:
    forming an ultra-thin gripping layer comprising an acrylic-based polymer on a glove-shaped former, said ultra-thin gripping layer being between about 0.25 and about 1.5 microns thick;
    contacting said ultra-thin gripping layer with a coagulant composition; and
    forming a base polymer layer on said ultra-thin gripping layer, said base polymer layer comprising an elastomeric material, said elastomeric material coagulating on said ultra-thin gripping layer upon contact of said elastomeric material with said coagulant composition.

20. The process of claim 19, further comprising forming a donning layer on said base polymer layer.

21. The process of claim 19, wherein said acrylic-based polymer is heated to a temperature of between about 35° C. and about 50° C. prior to forming said ultra-thin gripping layer.

22. The process of claim 19, wherein said base polymer layer is formed by immersing said glove-shaped former at least one time in a tank containing said elastomeric material.

23. The process of claim 22, wherein said base polymer layer is formed by immersing said glove-shaped former at least twice in a tank containing said elastomeric material.

24. The process of claim 19, wherein said base polymer layer is between about 3 and about 5.5 mils thick.

25. The process of claim 19, wherein the base polymer layer comprises a natural latex rubber.

26. The process of claim 19, wherein the base polymer layer comprises a nitrile polymer.

27. The process of claim 19, wherein the ultra-thin gripping layer is formed by dipping the former into an emulsion containing the acrylic-based polymer.

28. The process of claim 27, wherein the emulsion containing the acrylic-based polymer also contains a surfactant having an HLB between about 7 and about 11.

29. The process of claim 21, wherein said ultra-thin gripping layer is between about 0.5 and about 1.5 microns thick.

* * * * *